United States Patent

Souma et al.

Patent Number: 5,030,752
Date of Patent: Jul. 9, 1991

[54] FORMYLATED ALKYLBENZENESULFONYL HALIDE COMPOUND

[75] Inventors: Yoshie Souma, Ibaraki; Jun Iyoda, Ikeda; Hirosi Sano, Mino, all of Japan

[73] Assignee: Agency of Industrial Science & Technology, Tokyo, Japan

[21] Appl. No.: 384,386

[22] Filed: Jul. 25, 1989

[30] Foreign Application Priority Data

Sep. 13, 1988 [JP] Japan .................. 63-230388

[51] Int. Cl.$^5$ .......................................... C07C 309/86
[52] U.S. Cl. .............................. 562/826; 562/828; 562/829; 562/833
[58] Field of Search ............... 562/826, 828, 827, 829, 562/833

[56] References Cited

U.S. PATENT DOCUMENTS 2,680,134 6/1954 Gregory .................. 562/826
2,888,486 5/1959 Gregory .................. 562/833
4,051,168 9/1977 Feiring .................... 562/826

FOREIGN PATENT DOCUMENTS 520317 1/1956 Canada .
39-29760 12/1939 Japan .

Primary Examiner—Donald B. Moyer
Assistant Examiner—Margaret Argo
Attorney, Agent, or Firm—Armstrong, Nikaido, Marmelstein, Kubovcik & Murray

[57] ABSTRACT

A formylated alkylbenzenesulfonyl halide compound represented by the following general formula (I):

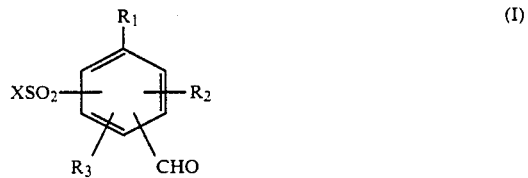

wherein $R_1$ is an alkyl group having 1 to 5 carbon atoms; $R_2$ and $R_3$ are each a member selected from the group consisting of a hydrogen atom and alkyl groups having 1 to 5 carbon atoms; X is a halogen atom; the sulfonyl halide group is present at the ortho or para position while the formyl group at the para or ortho position relative to the group $R_1$ when $R_2$ and $R_3$ are both a hydrogen atom, while the sulfonyl halide group and the formyl group are present at the para positions relative to the groups $R_1$ and $R_2$, respectively, when $R_2$ is an alkyl group and $R_3$ is a hydrogen atom, or the sulfonylhalide group and the formyl group are present at the para positions relative to the groups $R_1$ and $R_2$, respectively, when $R_2$ and $R_3$ are both an alkyl group; the compound (I) being prepared by reacting an alkylbenzene represented by the following formula (III) with carbon monoxide and a halosulfonic acid represented by the following formula (II) in the presence of an antimony halide:

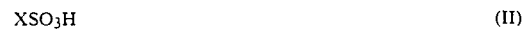

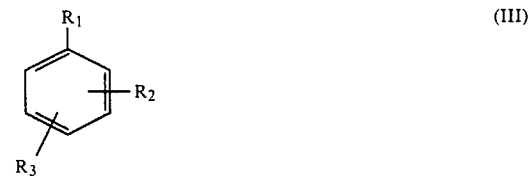

wherein all of X in the formula (II) and $R_1$, $R_2$ and $R_3$ in the formula (III) are as defined above.

2 Claims, No Drawings

FORMYLATED ALKYLBENZENESULFONYL HALIDE COMPOUND

BACKGROUND OF THE INVENTION

The present invention relates to a novel formulated alkylbenzenesulfonyl halide compound and a process for preparing the same. More particularly, the invention relates to a novel formulated alkylbenzenesulfonyl halide compound having a benzene ring substituted with a sulfonyl halide group and a formyl group at the ortho and para positions thereof, respectively, relative to an alkyl group, or at the para positions thereof relative to two alkyl groups, and a process for preparing the same under atmospheric pressure at ordinary temperature in one step.

Aromatic sulfonyl compounds are industrially important as intermediates for the syntheses of drugs, dyes, etc. and starting materials for the preparation of transparent polysulfone resins having a high -heat resistance.

Methods of introducing a sulfonyl group into an aromatic compound include one as disclosed in Japanese patent application Kokai publication No. 59-141556 wherein chlorobenzene is reacted with chlorosulfonic acid to synthesize 4-chlorobenzenesulfonyl chloride.

Meanwhile, methods of introducing a formyl group into an alkylbenzene include one as disclosed in Japanese patent publication No. 39-29760 wherein an alkylbenzene is reacted with carbon monoxide in the presence of hydrogen fluoride and boron trifluoride.

However, there are no known methods of introducing a sulfonyl group and a formyl group simultaneously into an aromatic compound.

SUMMARY OF THE INVENTION

A first object of the present invention is to provide a novel formylated alkylbenzenesulfonyl halide compound having a benzene ring substituted with a sulfonyl halide group and a formyl groups at the ortho and para positions thereof, respectively, relative to an alkyl group, or at the para positions thereof relative to two alkyl groups.

A second object of the present invention is to provide a process for preparing a formylated alkylbenzenesulfonyl halide compound of the kind as described above under atmospheric pressure at ordinary temperature in one step.

DETAILED DESCRIPTION OF THE PREFERRED EMBODIMENTS

The novel formylated alkylbenzenesulfonyl halide compound of the present invention is represented by the following general formula (I):

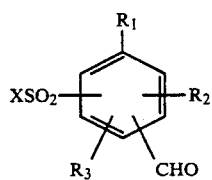

(I)

wherein $R_1$ is an alkyl group having 1 to 5 carbon atoms; $R_2$ and $R_3$ are each a member selected from the group consisting of a hydrogen atom and alkyl groups having 1 to 5 carbon atoms; X is a halogen atom; the sulfonyl halide group is present at the ortho or para position while the formyl group at the para or ortho position relative to the group $R_1$ when $R_2$ and $R_3$ are both a hydrogen atom, while the sulfonyl halide group and the formyl group are present at the para positions relative to the groups $R_1$ and $R_2$, respectively, when $R_2$ is an alkyl group and $R_3$ is a hydrogen atom, or the sulfonyl halide group and the formyl group are present at the para positions relative to the groups $R_1$ and $R_2$, respectively, when $R_2$ and $R_3$ are both an alkyl group.

Specific examples of the novel formylated alkylbenzenesulfonyl halide compound of the present invention include the following compounds enumerated under the respective compound No.

(1) 3-formyl-6-methylbenzenesulfonyl fluoride

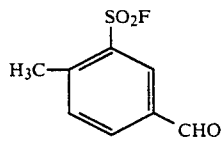

(2) 3-formyl-4-methylbenzenesulfonyl fluoride

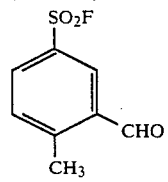

(3) 3-formyl-4,6-dimethylbenzenesulfonyl fluoride

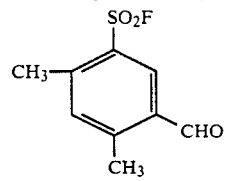

(4) 3-formyl-4,6-diethylbenzenesulfonyl fluoride

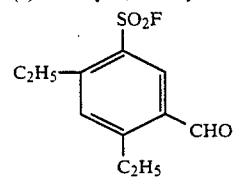

(5) 2-formyl-4,5-dimethylbenzenesulfonyl fluoride

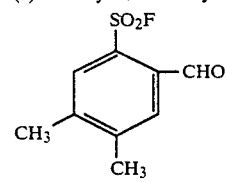

(6) 2-formyl-4,5-diethylbenzenesulfonyl fluoride

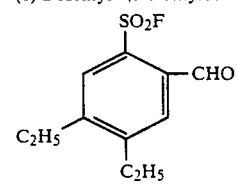

(7) 3-formyl-2,4,6-trimethylbenzenesulfonyl fluoride

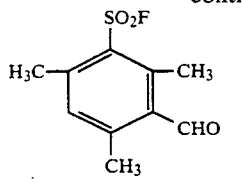

(8) 3-formyl-2,4,6-triethylbenzenesulfonyl fluoride

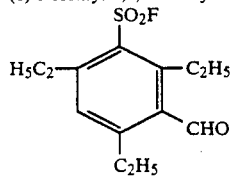

(9) 3-formyl-6-n-pentylbenzenesulfonyl fluoride

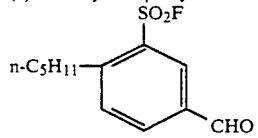

(10) 3-formyl-4,6-dimethylbenzenesulfonyl chloride

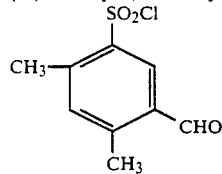

The novel compound of the present invention can be prepared by reacting an alkylbenzene represented by the following general formula (III) with carbon monoxide and a halosulfonic acid represented by the following general formula (II) in the presence of an antimony halide catalyst:

$$XSO_3H \qquad (II)$$

wherein X is a halogen atom, and

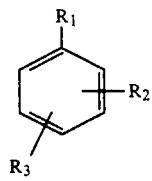

(III)

wherein $R_1$ is an alkyl group having 1 to 5 carbon atoms, and $R_2$ and $R_3$ are each a member selected from the group consisting of a hydrogen atom and alkyl groups having 1 to 5 carbon atoms.

When a halosulfonic acid is mixed with an antimony halide, a superacid, such as $[FSO_2+]+ [OH-]SbF_5$, is formed. The acid strength of such a superacid is at least 100 times as high as that of 100 % sulfuric acid. Therefore, the use of the superacid makes it possible to carry out reactions which cannot proceed in systems wherein sulfuric acid or polyphosphoric acid is used. Specifically, formyl cations [CHO ] and sulfonyl cations [$SO_2X+$] can be present stably in the superacid to be available for electrophilic attack on an aromatic compound to facilitate the occurrence of electrophilic substitution reactions thereof with the aromatic compound.

More specifically, sulfonyl cations and formyl cations attack the ortho and para positions, respectively, or two para positions, if present, of an alkylbenzene. One example of such reaction processes will be shown in the following reaction formula:

$$CO + H^+ \rightarrow [CHO\ ]$$

$$FSO_3H + SbF_5 \rightarrow [FSO_2^3] + [OH^-]SbF_5$$

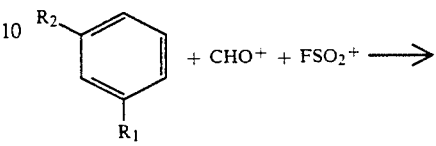

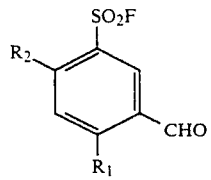

Thus, according to the process of the present invention, both sulfonation and carbonylation proceed readily and simultaneously merely by adding an alkylbenzene slowly to a mixture of a halosulfonic acid with an antimony halide in an atmosphere of carbon monoxide. After the completion of the reaction, the reaction mixture is poured into ice water and extracted with an organic solvent to give the desired formulated alkylbenzenesulfonyl halide in one step.

In the case of alkylbenzenes of the formula (III) wherein $R_2$ and $R_3$ are both a hydrogen atom, namely monoalkylbenzenes, compounds having sulfonyl halide and formyl groups introduced thereinto at the ortho and para positions relative to the alkyl group thereof, such as the aforementioned compounds Nos. 1, 2 and 9 are obtained by the process of the present invention.

Dialkylbenzenes of the formula (III) wherein $R_2$ is an alkyl group while $R_3$ is a hydrogen atom are classified into ones having the two alkyl groups at the meta positions relative to each other, and ones having the two alkyl groups at the ortho positions relative to each other. For example, the aforementioned compounds Nos. 3, 4 and 10 are obtained from the former type of dialkylbenzenes, while, for example, the aforementioned compounds Nos. 5 and 6 are obtained from the latter type of dialkylbenzenes.

In the case of trialkylbenzenes of the formula (III) wherein $R_2$ and $R_3$ are both an alkyl group, for example the aforementioned compounds Nos. 7 and 8 are obtained.

Specific examples of the alkylbenzene to be used in the present invention include monoalkylbenzenes such as toluene, ethylbenzene, butylbenzene, pentylbenzene, isopropylbenzene, and isobutylbenzene; 1,3-dialkylbenzenes such as m-xylene, 1,3-diethylbenzene, 1-ethyl-3-methylbenzene, 1,3-dibutylbenzene, and 1,3-dipentylbenzene; 1,2-dialkylbenzenes such as o-xylene, 1,2-diethylbenzene, 1,2-dipropylbenzene, and 1,2-dipentylbenzene; and 1,3,5-trialkylbenzenes such as 1,3,5-trimethylbenzene and 1,3,5-triethylbenzene.

Fluorosulfonic acid, chlorosulfonic acid, etc. are usable as the halosulfonic acid, while antimony pentafluoride, antimony pentachloride, etc. are usable as the antimony halide.

The molar ratio of the starting materials to the catalyst is such that alkylbenzene : halosulfonic acid : antimony halide = 1 : [0.2~10]:[0.2~5].

Mere replacement of the air in a reactor with carbon monoxide will suffice to provide the atmosphere of carbon monoxide, and it is not always necessary to blow carbon monoxide into a reaction mixture or to pressurize the reactor with carbon monoxide.

Ordinary temperature will suffice as the reaction temperature, though it may be raised up to 60° C. The reaction time ranges from about 2 to about 24 hours.

Since the viscosity of the reaction mixture increases in keeping with the progress of the reaction, it is preferable to use a solvent such as trifluoroacetic acid, trichloroacetic acid, dichloroacetic acid, sulfuric acid or acetic anhydride, the use of which permits the reaction to proceed smoothly.

The resulting product was subjected to NMR, IR and mass spectrometric analyses to confirm that it is a novel compound.

As described hereinbefore, all of the formulated alkylbenzenesulfonyl halide compounds according to the present invention are novel compounds. These compounds are useful as starting materials of drugs, dyes, engineering plastics, etc.

Further, according to the process of the present invention, a formyl group and a sulfonyl group can be simultaneously introduced into an alkylbenzene molecule under atmospheric pressure at ordinary temperature to give the desired compound in one step.

The following Examples will illustrate the present invention in more detail.

EXAMPLE 1

Preparation of 3-formyl-6-methylbenzenesulfonyl fluoride (compound No. 1) and 3-formyl-4-methylbenzenesulfonyl fluoride (compound No. 2)

A three-necked flask connected with a carbon monoxide gas buret is purged with carbon monoxide through the buret and charged with 20 ml of fluorosulfonic acid, 10 ml of antimony pentafluoride and 10.6 ml of toluene. The reaction was effected under stirring at 25° C. for 8 hours. The molar ratio of toluene : fluorosulfuric acid : antimony pentafluoride was 1 : 3.5 : 1.4, while the consumption of carbon monoxide was 2.24 λ.

After the completion of the reaction, the reaction mixture was poured into ice water and extracted with benzene, which was then removed from the extract. The remaining oily substance was subjected to gas chromatographic, NMR, IR, and mass spectrometric analyses to confirm the formation of 3.03 g of 3-formyl-6-methylbenzenesulfonyl fluoride (compound No. 1) in a yield of 15 % based on toluene.

The physical properties of the compound No. 1 are as follows:

mass spectrum: $M^+(m/e) = 202$.

$^1H$ NMR chemical shift δ (CCl4): 2.74 (3H, s) 7.50 (1H, d) 8.00 (1H, d) 9.88 (1H, s)

IR spectrum ($cm^{-1}$): 1715, 1600, 1420, 1220, 770.

It was also confirmed through the analyses that isomeric 3-formyl-4-methylbenzenesulfonyl fluoride (compound No. 2) was formed in a yield of 5 % based on toluene.

The physical properties of the compound No. 2 are as follows:

mass spectrum: $M^+(m/e) = 202$.

$^1H$ NMR chemical shift δ (CCl4) 2.78 (3H, s), 7.45 (1H, d) 7.95 (1H, d), 8.22 (1H, d) 10.20 (1H, s).

IR spectrum ($cm^{-1}$): 1700, 1600, 1410, 1180, 1220.

EXAMPLE 2

Preparation of 3-formyl-4,6-dimethylbenzenesulfonyl fluoride (compound No. 3)

A three-necked flask purged with carbon monoxide in the same manner as that of Example 1 was charged with 20 ml of fluorosulfonic acid, 10 ml of antimony pentafluoride, and trifluoroacetic acid as a solvent, to which 12.2 ml of m-xylene was slowly added at 25° C. The reaction was effected under stirring at 25° C. for 6 hours. The molar ratio of m-xylene : fluorosulfonic acid : antimony pentafluoride was 1 : 3.5 : 1.4, while the consumption of carbon monoxide was 2.23 λ. The reaction mixture was treated in the same manner as that of Example 1 to give an oily product, which was then subjected to the same analyses as those of Example 1 to confirm the formation of 3-formyl-4,6-dimethylbenzenesulfonyl fluoride (compound No. 3) in a yield of 83 % based on m-xylene. The physical properties of the compound No. 3 are as follows:

mass spectrum: $M^+(m/e) = 216$.

$^1H$ NMR chemical shift δ (CDCl3) 2.71 (3H, s) 2.74 (3H, s) 7.35 (1H, s) 8.41 (1H, s) 10.23 (1H, s). $^{13}C$ NMR chemical shift δ (CDCl3) 19.6, 20.4, 131.1, 133.6, 134.0, 136.6, 143.4, 148.1, 189.9

IR spectrum ($cm^{-1}$): 1690, 1600, 1410, 1380, 1260, 1180, 770, 650.

Melting point: 68.5~70° C.

EXAMPLE 3

Preparation of 3-formyl-4,6-diethylbenzenesulfonyl fluoride (compound No. 4)

12.48 ml of 1,3-diethylbenzene was reacted with 20 ml of fluorosulfonic acid in a carbon monoxide atmosphere in the presence of 10 ml of antimony pentafluoride under stirring at 25° C. for 8 hours in substantially the same manner as that of Example 1. The molar ratio of 1,3-diethylbenzene : fluorosulfonic acid : antimony pentafluoride was 1 : 4.4 : 1.7, while the consumption of carbon monoxide was 1,800 ml. The reaction product was extracted in the same manner as that of Example 1 and then subjected to the same analyses as those of Example 1 to confirm the formation of 11.8 g of 3-formyl-4,6-diethylbenzenesulfonyl fluoride (compound No. 4) in a yield of 60 % based on 1,3-diethylbenzene.

mass spectrum: $M^+(m/e) = 244$.

$^1H$ NMR chemical shift δ (CCl4) 10.05 (1H, s) 8.23 (1H, s) 7.31 (1H, s) 3.11 (2H, q) 3.03 (2H, q) 1.33 (3H, t) 1.28 (3H, t)

IR spectrum ($cm^{-1}$): 2980, 1700, 1600, 1410, 1210, 765.

EXAMPLE 4

Preparation of 2-formyl-4,5-dimethylbenzenesulfonyl fluoride (compound No. 5)

7.2 ml of o-xylene was reacted with 20 ml of fluorosulfonic acid in a carbon monoxide atmosphere in the presence of 10 ml of antimony pentafluoride under stirring at 25° C. for 8 hours in substantially the same manner as that of Example 1. The molar ratio of o-xylene : fluorosulfonic acid : antimony pentafluoride was 1 : 5.9 : 2.37, while the consumption of carbon monoxide was 1,340 ml. The reaction product was extracted in the same manner as that of Example 1 and then subjected to the same analyses as those of Example 1 to confirm the formation of 2.6 g of 2-formyl-4,5-dimethylbenzenesulfonyl fluoride (compound No. 5) in a yield of 20 % based on o-xylene.

mass spectrum: M+(m/e)=216:

$^1$H NMR chemical shift δ (CCl$_4$): 2.70 (6H, s) 8.00 (1H, s) 8.35 (1H, s) 10.09 (1H, s)

IR spectrum (cm$^{-1}$): 1700, 1600, 1420, 1210, 770.

EXAMPLE 5

Preparation of 2-formyl-4,5-diethylbenzenesulfonyl fluoride (compound No. 6)

7.7 ml of 1,2-diethylbenzene was reacted with ml of fluorosulfonic acid and carbon monoxide in the presence of 12.6 ml of antimony pentafluoride and 10 ml of chloroacetic acid as a solvent at 25° C. for 8 hours in substantially the same manner as that of Example 1. The molar ratio of 1,2-diethylbenzene : fluorosulfonic acid : antimony pentafluoride was 1 : 7 : 2, while the consumption of carbon monoxide was 1,120 ml. The reaction product was extracted in the same manner as that of Example 1 and then subjected to the same analyses as those of Example 1 to confirm the formation of 1.2 g of 2-formyl-4,5-diethylbenzenesulfonyl fluoride (compound No. 6) in a yield of 10 % based on 1,2-diethylbenzene.

mass spectrum: M+ (m/e)=244. $^1$H NMR chemical shift δ (CCl$_4$): 1.25 (6H, t) 2.40∼3.3 (4H, m) 7.0 (1H, s) 7.8 (1H, s) 10.0 (1H, s)

IR spectrum (cm$^{-1}$): 2980, 1700, 1600, 1210.

EXAMPLE 6

Preparation of 3-formyl-2,4,6-trimethylbenzenesulfonyl fluoride (compound No. 7)

18.9 ml of 1,3,5-trimethylbenzene was reacted with 20 ml of fluorosulfonic acid and carbon monoxide in the presence of 10 ml of antimony pentafluoride and 10 ml of trifluoroacetic acid as a solvent at 20° C. for 48 hours in substantially the same manner as that of Example 1. The molar ratio of 1,3,5-trimethylbenzene : fluorosulfonic acid : antimony pentafluoride was 1 : 3.5 : 1.4, while the consumption of carbon monoxide was 2.24 λ. The same analyses as those of Example 1 were made to confirm the formation of 6.9 g of 3-formyl-2,4,6-trimethylbenzenesulfonyl fluoride (compound No. 7) in a yield of 30 % based on 1,3,5-trimethylbenzene. mass spectrum: M+(m/e)=230.

$^1$H NMR chemical shift δ (CDl$_3$): 2.50 (3H, s), 2.65 (3H, s) 2.71 (3H, s), 6.95 (1H, s) 10.58 (1H, s), IR spectrum (cm$^{-1}$): 3000, 1700, 1590, 1400, 1205, 760.

EXAMPLE 7

Preparation of 3-formyl-2,4,6-triethylbenzenesulfonyl fluoride (compound No. 8)

9.3 ml of 1,3,5-triethylbenzene was reacted with 20 ml of fluorosulfonic acid and carbon monoxide in the presence of 10 ml of antimony pentafluoride at 35° C. for 8 hours in substantially the same manner as that of Example 1. The molar ratio of 1,3,5-triethylbenzene : fluorosulfonic acid : antimony pentafluoride was 1 : 7 : 2.8, while the consumption of carbon monoxide was 1.13 λ. The same analyses as those of Example 1 were made to confirm the formation of 1.36 g of 3-formyl-2,4,6-triethylbenzenesulfonyl fluoride (compound No. 8) in a yield of 10 % based on 1,3,5-triethylbenzene.

mass spectrum: M+(m/e)=272.

$^1$H NMR chemical shift δ (CCl$_4$): 1.3 (9H, m), 2.0 (6H, m), 7.4 (1H, s) 10.1 (1H, s)

IR spectrum (cm$^{-1}$): 1700, 1410, 1200.

EXAMPLE 8

Preparation of 3-formyl-6-n-pentylbenzenesulfonyl fluoride (compound No. 9)

8.6 ml of n-pentylbenzene was reacted with 20 ml of fluorosulfonic acid and carbon monoxide in the presence of 10 ml of antimony pentafluoride at 35° C. for 8 hours in substantially the same manner as that of Example 1. The molar ratio of n-pentylbenzene : fluorosulfonic acid : antimony pentafluoride was 7.0 : 2.8, while the consumption of carbon monoxide was 450 ml. The same analyses as those of Example 1 were made to confirm the formation of 1.36 g of 3-formyl-6-n-pentylbenzenesulfonyl fluoride (compound No. 9) in a yield of 10 % based on n-pentylbenzene.

mass spectrum: M+(m/e)=258.

$^1$H NMR chemical shift δ (CCl$_4$): 1.2 (3H, t), 1.7 (4H, m), 2.6 (4H, m), 7.0∼8.0 (3H, m), 9.9 (1H, s) IR spectrum (cm$^{-1}$): 1710, 1410, 1220.

EXAMPLE 9

Preparation of 3-formyl-4,6-dimethylbenzenesulfonyl chloride (compound No. 10)

6.1 ml of m-xylene was reacted with 20 ml of chlorosulfonic acid and carbon monoxide in the presence of 10 ml of antimony pentafluoride at 30° C. for 10 hours in substantially the same manner as that of Example 1. The molar ratio of m-xylene : chlorosulfonic acid : antimony pentafluoride was 1 : 6.2 : 2.8, while the consumption of carbon monoxide was 900 ml. The same analyses as those of Example 1 were made to confirm the formation of 0.6 g of 3-formyl-4,6-dimethylbenzenesulfonyl chloride (compound No. 10) in a yield of 5 % based on m-xylene.

mass spectrum: M+(m/e)=232.

IR spectrum (cm$^{-1}$): 1710, 1410, 1200, 700.

What is claimed is:

1. A formylated alkylbenzenesulfonyl halide compound represented by the following formula (I):

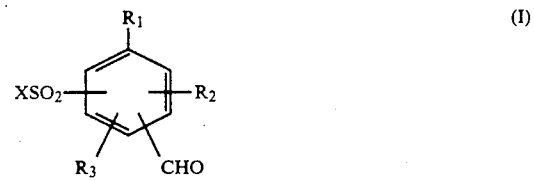

wherein $R_1$ is an alkyl group having 1 to 5 carbon atoms; $R_2$ and $R_3$ are each a member selected from the group consisting of a hydrogen atom and alkyl groups having 1 to 5 carbon atoms; X is a halogen atom; the sulfonyl halide group is present at the ortho or para position and the formyl group at the para or ortho position relative to said group $R_1$ when $R_2$ and $R_3$ are both a hydrogen atom; and the sulfonyl halide group and the formyl group are present at the para positions relative to said groups $R_1$ and $R_2$, respectively, when $R_2$ is an alkyl group and $R_3$ is a hydrogen atom; or the sulfonyl halide group and the formyl group are present at the para positions relative to said groups $R_1$ and $R_2$, respectively, when $R_2$ and $R_3$ are both an alkyl group.

2. A formylated alkylbenzenesulfonyl halide compound as claimed in claim 1, wherein X is a member selected from the group consisting of a fluorine atom and a chlorine atom.

* * * * *